United States Patent
Kazandjian et al.

(10) Patent No.: US 6,920,346 B2
(45) Date of Patent: Jul. 19, 2005

(54) PRE-OPERATIVE DEVICE FOR LOCALIZING MARKED TISSUES AND PROCESS USING SUCH A DEVICE

(75) Inventors: Anne Kazandjian, Chennevieres sur Marne (FR); Jacques Chambron, Strasbourg (FR)

(73) Assignee: Eurorad 2-6 (Societe Anonyme), Strasbourg Cedex (FR)

( * ) Notice: Subject to any disclaimer, the term of this patent is extended or adjusted under 35 U.S.C. 154(b) by 408 days.

(21) Appl. No.: 10/119,219

(22) Filed: Apr. 10, 2002

(65) Prior Publication Data

US 2002/0147393 A1 Oct. 10, 2002

(30) Foreign Application Priority Data

Apr. 10, 2001 (FR) .............................. 01 04901

(51) Int. Cl.⁷ ................................. A61B 5/05
(52) U.S. Cl. .................. 600/420; 600/407; 600/414; 600/426; 600/431; 600/436; 600/473; 600/476; 424/9.3; 250/363.01; 250/302; 324/309
(58) Field of Search ................. 600/407–482; 424/9.3; 250/302, 363.1, 363.01; 324/309

(56) References Cited

U.S. PATENT DOCUMENTS

| | | |
|---|---|---|
| 4,995,396 A | 2/1991 | Inaba et al. |
| 5,088,492 A | 2/1992 | Takayama et al. |
| 5,694,933 A * | 12/1997 | Madden et al. ............. 600/431 |
| 5,800,350 A | 9/1998 | Coppleson et al. |
| 6,026,316 A * | 2/2000 | Kucharczyk et al. ....... 600/420 |
| 6,171,796 B1 * | 1/2001 | An et al. ....................... 435/6 |

FOREIGN PATENT DOCUMENTS

WO    WO 98/52064    11/1998

OTHER PUBLICATIONS

Database WPI Section PQ, Week 199843 Derwent Publications Ltd., London, GB; AN 1998–499248; XP002187562 & JP 10 216072 A (Olympus Optical Co LTD), 18 aout 1998. (Aug. 18, 1998).

* cited by examiner

*Primary Examiner*—Brian L. Casler
*Assistant Examiner*—William C Jung
(74) *Attorney, Agent, or Firm*—Young & Thompson

(57) ABSTRACT

A pre-operative device includes at least one elongated probe (1) integrating at least one element for detecting radioactive radiation (3) emitted by tissues (4) marked by radioactive isotopes or radioactive colloids, generating a first representative electrical signal (5), at least one element (6) for emitting luminous radiation toward the tissues (4) and at least one element (7) for receiving and transmitting reflected luminous radiation (8) reflected by the tissues (4) marked by vital colorants or magnetic markers, toward at least one element (9) for converting the reflected luminous radiation (8) into a second representative electrical signal (10), electrical connection elements for conveying the first and second electrical signals (5, 10) and, at least one electronic means (11) for processing electronic signals.

20 Claims, 1 Drawing Sheet

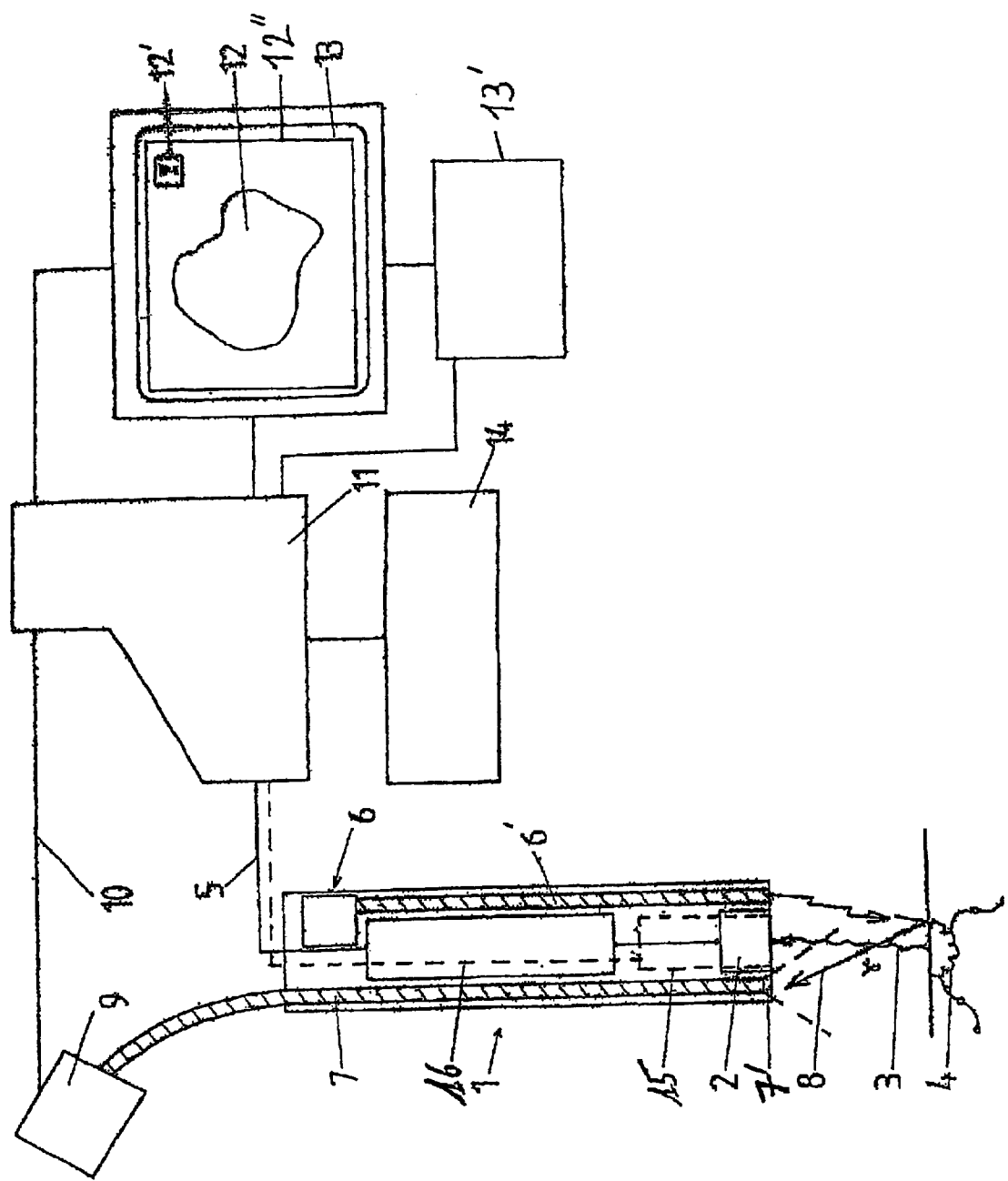

PRE-OPERATIVE DEVICE FOR LOCALIZING MARKED TISSUES AND PROCESS USING SUCH A DEVICE

BACKGROUND OF THE INVENTION

The present invention relates to the field of medical technique for the location of tumors or the like, more particularly devices and probes adapted to be used on or introduced into the human body.

It has for its object a pre-operative location device for marked tissues, particularly by radioactive isotopes of superparamagnetic substances and/or by vital colorants, particularly for the detection and identification of lymphatic ganglia, as well as a process using said device.

The location of marked tissues with the help of isotopes emitting gamma radiation is known for the excision of cancerous tissues as well as for the identification of lymphatic ganglia called "hots".

The auxiliary ganglia are for example excellent indicators of the prognosis and treatment to be used in the field of melanomas and of breast cancer.

However, the location of the so-called "sentinel" ganglion often gives rise to difficulties, particularly because of its proximity to the principal tumor.

Present devices of the nuclear type, although relatively sensitive, however do not permit a percentage of detection greater than 80%.

Another approach to the location of cancerous tissues consists in injecting a vital colorant which has the property of accumulating in the ganglia, then detecting the presence of regions strongly concentrated in colorant in the patient. This detection is at present carried out by visual observation of the resulting colored regions.

However, this second method has several drawbacks connected, on the one hand, to the nature itself of the colorants used (selectivity as to the tumor; retention time; troublesome indelible coloration of the visible tissues because of the necessary concentrations, particularly in cutaneous cancers, in breast cancers; cost . . . ) and, on the other hand, their use (determination of the injection point, of the paths of diffusion, precision of detection . . . )

As a result, there does not at present exist location apparatus which will be both very sensitive (percent of location greater than 95%), which has good spatial resolution, and which will be more capable of differentiating the primary radiations from the diffused radiations.

SUMMARY OF THE INVENTION

The present invention has for its object to overcome particularly all of the mentioned drawbacks.

To this end, it has for its object a device for the pre-operative location of marked tissues, in particular for the location of tumors, characterized in that it comprises essentially, on the one hand, at least one probe having preferably an elongated shape and integrating at least two of the three types of detection means selected from the group formed by:

at least one detection means of radioactive radiation emitted by tissues marked with isotopes or radioactive colloids, generating a corresponding representative electrical signal;

at least one optical detection means comprising at least one means for emitted luminous radiation toward the tissues and at least one means for receiving and transmitting luminous radiation reflected or emitted by fluorescence or luminescence by said marked tissues, by vital colorants, toward at least one conversion means of said recovered luminous radiation, as a corresponding electrical signal;

detection means for supplying or measuring the magnetic susceptibility in the marked tissues by superparamagnetic substances, such as ferromagnetic colloids and/or ferrofluids, generating a corresponding representative electrical signal;

on the other hand, means for transmitting or conveying the mentioned electrical signals, and, finally, at least one electronic means for processing the electrical signals conveyed by the dimensioned means, for the display, superimposition, inlaying and/or editing of a reconstituted image, at least partial, of tissues marked by said colorants and, simultaneously, supplying a perceptible physical expression of the representative electrical signal delivered by the detection means of radioactive radiation emitted by the radioactively marked tissues and/or of the representative electrical signal delivered by the means for detecting the supply or measuring the magnetic susceptibility of the marked tissues by superparamagnetic substances.

It also has for its object a process for localizing tissues previously marked with the help of radioactive isotopes, with the help of vital colorants and/or with the help of superparamagnetic substances, in particular for the location of tumors, using the device described above, characterized in that it comprises essentially the following steps:

carrying out a first empirical marking of the zone or zones of tissues to be examined, producing a first series of reconstituted images of the tissues marked by said colorants in the zone or zones previously designated or in the suspected zone or zones, so as to determine the approximate contours of said zone or zones to be examined or in detail, within the previously determined contours, proceeding with a series of measurements, by the detection of the radioactive radiation emitted by said radioactively marked tissues and/or the detection of the supply or measurement of the magnetic susceptibility of said magnetically marked tissues, so as to determine more precise contours for the zones having peaks of radioactivity and/or magnetic characteristics, and producing a second series of reconstituted images of the marked tissues in the zone or zones determined in the preceding step so as to obtain one or more reconstituted images with precise contours of said zone or zones of marked tissues, particularly for the display, temporary storage, editing, filing and/or ultimate processing, for example electronic, of said reconstituted image or images and of the visual expression or expressions of the signal or of the representative signal or signals.

The invention will be better understood from the following description, which relates to a preferred embodiment, given by way of non-limiting example, and explained with reference to the accompanying schematic drawing, whose FIGURE is a diagram of the principle of the device according to one possible embodiment of the invention.

BRIEF DESCRIPTION OF THE DRAWING

FIG. 1 is a schematic view of a device for the pre-operative location of marked tissues, in particular for the location of tumors.

DETAILED DESCRIPTION OF THE PREFERRED EMBODIMENT

According to the invention, this device comprises essentially, on the one hand, at least one probe 1 preferably having an elongated shape and integrating at least two of the three types of detection means 2; 6, 7; 15 selected from the group formed by:

at least one means 2 for the detection of radioactive radiation 3 emitted by tissues 4 marked with isotopes or radioactive colloids, generating a corresponding representative electrical signal 5;

at least one optical detection means comprising at least one means 6 for emitting luminous radiation toward the tissues 4 and at least one means 7 for receiving and transmitting luminous radiation 8 reflected or omitted by fluorescence or luminescence by said tissues 4 marked with vital colorants, toward at least one conversion means 9, of said recovered luminous radiation 8, as a corresponding electrical signal 10;

a means 15 for the detection of the supply or the measurement of magnetic susceptibility of the tissues 4 marked with superparamagnetic substances, such as ferromagnetic colloids and/or ferrofluids, generating a corresponding representative electrical signal 16;

on the other hand, means for transmitting or conveying the mentioned electrical signals 5, 10, 16 and, finally, at least one electronic means 11 for processing the electrical signals 5, 10, 16 supplied by the mentioned means, for the display, superimposition, inlaying and/or editing of a reconstituted image 12, at least partially, of tissues 4 marked by said colorants and, simultaneously, supplying a perceptible physical expression 12' of the representative electrical signal 5 delivered by the means 2 for the detection of the radioactive radiation 3 emitted by the radioactively marked tissues 4 and/or of the representative electrical signal 16 delivered by the means 15 for detecting the magnetization or for measuring the electrical susceptibility of the tissues 4 marked by the superparamagnetic substances.

There is meant by "vital" colorant any substance useful for the coloration of certain mentioned tissues 4, in particular living tissues, particularly normal human tissues or tissues having structural or functional anomalies of the cells constituting them (excessive or uncontrolled proliferation of the type of cancer, mutations, degradations, necroses . . . ), to the end of detecting and/or localizing said tissues 4 by designating the regions in which said colorant is fixed to said tissues 4 thereby creating a zone of elevated concentration of colorant, greater than that present in the other healthy tissues.

According to a first embodiment, the probe 1 can comprise a means 2 for the detection of radioactive radiation 3 and at least one optical detection means 6, 7.

According to a second embodiment, the probe 1 can comprise a means 15 for detecting magnetization or for measuring magnetic susceptibility and at least one optical detection means 6, 7.

According to a third preferred embodiment of the invention, the probe 1 can comprise a means 2 for detecting radioactive radiation 3, a means 15 for measuring magnetic susceptibility and at least one optical detection means 6, 7.

The device according to the invention could if desired comprise a set of interchangeable probes 1 corresponding each to one of the above embodiments, each of these probes 1 being if desired used as a function of the difficulty of detection that is anticipated, of the nature of the tissues to be examined or of the type of examination to be carried out. The simultaneous use of means 2, 15 and 6, 7 will permit detection with a very high reliability using three types of detections combined with each other, which is to say associated physically and whose results can be intercorrelated.

In a particularly advantageous way, the device according to the invention comprises moreover a storage means 14, in digital form, for the data relative to one or several reconstituted images 12 and to said representative electrical signals 5, 16 generated simultaneously, on an electronic storage support, such as a computer memory, as well as if desired data relating to one or more anatomical images 12" of the operative field enclosing the marked tissues 4, taken before hand or subsequently.

Such a computer memory 14 can for example be a hard disk or an external memory of a workstation or of an individual computer. Such storage devices 14, permanent or not, for computer data are known as such and will not be described in greater detail.

Thanks to this characteristic, it becomes possible to establish an individual file for each patient in which are stored all the data on all the analyses, examinations and controls which the latter will have undergone over time. The access to these files can permit comparisons between different patients, following the development of the condition of the patient, the appreciation of the possible impact of treatments on this condition.

The electronic storage of data also permits easier material transport of large quantities of information, for example in the form of computer diskettes or CD-ROM, and gives the possibility of enjoying all the advantages of a transmission of said data by electronic means, particularly by electronic courier.

Similarly, there can also be envisaged the use of the above information as elements of proof, for example in the scope of litigation between the patient and the doctor.

As schematically shown in the accompanying FIGURE, the elongated probe 1 is generally in the form of a substantially cylindrical tube (straight or with a head portion inclined relative to the body) in which are disposed the detection means 2 of the radioactive radiation 3 emitted by said radioactively marked tissues 4 and/or the means 15 for detecting the magnetization or for measuring the magnetic susceptibility emitted by these same tissues 4 (also magnetically marked), as well as the emission means 6 of luminous radiation and the transmission means 7 of the luminous radiation 8 reflected by the tissues 4 marked moreover by vital colorants.

The radioactive markers used in the scope of the invention conventionally emit gamma rays (x-rays) such that according to another characteristic, the detection means 2 of the radioactive radiation 3 is a gamma ray detector (x-ray detector). Any detector conventionally used for this purpose can serve, such as, for example, a counter of the "Geiger Müller" type, with a solid ionization chamber (semiconductor) or with scintillation (cesium iodide or sodium iodide) coupled to a photodiode or to a photomultiplier.

Similarly, specific detectors with other types of radiation (alpha, beta . . . ) from the radioactive markers emitting these types of radiation, can also be used in the scope of the present invention, in addition to or in place of the detector 3 of gamma rays.

According to the principles of operation of such a "Geiger-Müller" counter and of a magnetic detector, the detection means 2 and the detection or measuring means 15 produce, thanks to known electronics, respectively an electrical signal 5 or 16 which is transmitted to at least one processing means 11 where it will be transformed into a signal or a physically perceptible expression 12' by the operator (if desired a different expression for each signal), for example in the form of a luminous indication, a graph, a number, a sonic bip, a vibration, etc., whose intensity, volume or size is preferably a function of the intensity of the detected radiation (for example proportional).

Thus, according to a first preferred modification, the physically perceptible expression 12' of the representative electric signal or signals 5, 16, simultaneously with the display of the reconstituted image 12, takes place in a sonic manner, for example with a loudspeaker or the like.

This sonic signal can, for example, be a continuous sound whose frequency or intensity (sonic level measured in dB) varies proportionally with the value of the measured radioactivity (signal modified as to frequency or amplitude or FM or respectively AM modes) or a discontinuous sound (bips) whose frequency is also proportional to the intensity of the measured radiation.

According to a second modified embodiment of the invention, the physically perceptible expression 12' of the representative electric signal or signals 5, 16, simultaneously with the display of reconstituted image 12, takes place in a visual manner, for example by the display or editing of said reconstituted image 12 and if desired the corresponding anatomical image 12".

Said visual signal can for example consist in a luminous strip whose filling of the illuminated portion gives a value proportional to the intensity of measured radioactivity or a bi-dimensional image of the distribution of radioactivity in a display or coordinates provided with an origin and axes graduated on the abscissa and ordinate.

In a particularly practical manner, the physically perceptible expression 12' of the representative electric signal or signals 5, 16, simultaneously with the display of the reconstituted image 12, takes place on the screen 13 serving to display said reconstituted image 12 and if desired the corresponding anatomical image 12".

By way of illustrative example, a graphic representation (in the form of an alert signal) has been provided as a physically perceptible signal 12' of the first electrical signal 5 on said screen 13 schematically represented in the accompanying drawing.

In this way, and thanks to the correlation of the two optical and nuclear measurements, the operator has, in the same instrument, both the two pieces of information simultaneously measured and can locate very easily and precisely the zone or zones of marked tissue 4 of interest.

The first representative electrical signal 5 can be correlated to the second electrical signal 10 obtained by optical detection, as well as if desired with the third representative signal 16, in the processing means 11 described in greater detail hereafter.

As to the emission means 6, a device according to the invention is particularly advantageous and is characterized in that the luminous emission means 6 is a laser.

Preferably, the laser used works in a range of wavelengths comprised between 4,000 and 10,000 angstroms.

In this case, the so-called "optical" measurements can take place in the microwave range, the visible radiation range and/or the infrared range (more particularly the near infrared).

As shown in the accompanying FIGURE, the luminous radiation emitted by the emission means 6 can first pass by an optical fiber or similar transmission means 6' adapted to the luminous radiation, from the source of emission (laser 6) to the analysis end of the elongated probe 1, in which the luminous radiation leaves this latter in the direction of the tissues 4 to be irradiated.

The radiation reflected (luminous reflected radiation 8) by said tissues 4 is then detected by a suitable optical detecting device (lens or suitable focusing means) mounted at the mentioned end (head) of the probe 1 and gathered and conveyed by at least one reception and transmission means 7 to a conversion means 9 for said reflected luminous radiation 8, into a second electrical signal 10.

As can be seen in the accompanying drawing, the reception and transmission means 7 of the luminous radiation 8 reflected by the marked tissues 4 is preferably an optical fiber or a bundle of fibers, at least partially, and preferably entirely, integrated into the elongated probe 1 and associated with a detecting or optical focusing device 7', such as for example a lens.

This permits locating the conversion means 9 outside the elongated probe 1, which thus will enable reduced dimensions facilitating its manipulation and permitting, as the case may be, its introduction into the body of the patient.

However, as a function of its nature and its size, said means 9 could also be integrated into the body of said probe 1 or else into the casing enclosing the electronic means 11.

Preferably, the conversion means 9 of said reflected luminous radiation 8 into a second electrical signal 10 is a CCD camera (Charge-Coupled Device: photosensitive device for transferring charges) or a luminous radiation detector of the opto-electronic converter type, as the case may be associated with a photomultiplier.

Conventional electrical connection means are of course provided and transmit said first, second and third electrical signals 5, 10, 16 to the electronic means 11 for processing said signals. These connection means could be of a filamentary nature (flexible cable) or radiofrequency (wireless), the probe 1 and the means 11 being in this latter case provided with suitable emission/reception means.

Preferably, the electronic means 11 for processing said electrical signals 5, 10 for their display, preferably in real time, of a reconstituted image 12 of the marked tissues 4 on a screen 13, if desired by superimposition of an anatomical image 12" separately acquired (for example by a CCD camera), is a computer workstation.

Such a workstation (or computer) 11 is known per se and comprises particularly a central unit provided with programs and software necessary for its use as well as all conventional data input and output means. Thanks to said workstation, the measured data can be processed in any useful way (statistical computation, addition of supplemental data or control of information thought to be useless . . . ), transformed so as to modify its presentation (representation in graphic form, images in several dimensions . . . ) or to facilitate its transmission, printing (by a corresponding means 13') or storage, etc., carried out by means of known suitable peripherals.

In particular, and in a particularly preferred manner, the electronic storage means 14 for data relative to one or several reconstituted images 12 and to the created electrical signals 5, 16, is that of said workstation.

According to another characteristic of the invention, the computer workstation 11 is moreover provided with printing means 13' for the reconstituted images 12 and/or for the process data relating to the first electrical signal 5 and/or to the third electrical signal 16.

According to a particularly preferred embodiment of the invention, the elongated probe 1 is an endoscopic probe.

The present invention also has for its object a process for locating tissues marked with radioactive isotopes, with vital colorants and/or with superparamagnetic substances, in particular for the location of tumors, using the device described above.

This process is characterized in that it comprises essentially the following steps:

carrying out a first empirical marking of the zone or zones of tissues 4 to be examined, producing a first series of reconstituted images 12 of the tissues 4 marked by said colorants in the zone or zones previously determined or in the suspected zone or zones, so as to determine the approximate contours of said zone or zones to be examined in greater detail, within previously predetermined contours, proceeding with a series of measurements, by the detection of radioactive radiation 3 emitted by said radioactively marked tissues 4 and/or the detection of magnetization or of measurement of the magnetic susceptibility in the magnetically marked tissues 4, so as to determine more precisely the contours of the zones having peaks of radioactivity and/or of magnetic characteristics, and producing a second series of reconstituted images 12 of the marked tissues 4 in the zone or zones determined in the preceding step so as to obtain one or more reconstituted images 12 with the precise contours of said zone or zones of marked tissues 4, particularly for the display, temporary storage, editing, of a file and/or of an ulterior treatment, for example electronic, of the said reconstituted image or images 12 and of the visual expression or expressions 12' of the representative signal or signals 5, 16.

The paths of injection of markers and the design of the device according to the invention can depend on the paths of surgical access to the organs and their tumors and are easily adaptable case by case by those skilled in the art. Accordingly, the steps of preparation of the patient will not be described in greater detail.

The first marking can be carried out by a professional, for example a qualified operator of the device according to the invention, particularly but not necessarily a doctor.

According to a first modified process according to the invention, the first empirical marking takes place in a manner visible to the naked eye.

According to a second modification, the first empirical marking can also take place by palpation of the tissue regions. Of course, it is also possible to combine these two approaches, palpation thus constituting a second empirical marking.

So as to give information directly usable by the doctor, the process can constitute also carrying out the taking of anatomical images 12" of the operative field enclosing the zone of tissues to be examined and particularly the marked tissues 4 to be localized, before taking the first series of reconstituted images 12 or after taking the second series of reconstituted images 12, these latter, as well as if desired the visible expression or expressions 12' of the representative electrical signal or signals 5, 16, being added by inlaying or superimposition on said anatomical image or images 12".

The process of the present invention is particularly adapted to localize precisely ganglia present in patients having tumors, having already been diagnosed as leading to cancer and if desired permits following its development.

With the help of specific markers, said process also permits detecting primary or secondary tumors.

Thanks to the combination of the two or three analysis processes by optical, nuclear and/or magnetic paths, the precise location of said tumors can be carried out in a certain manner in about 99% of the cases, which represents a significant improvement relative to the processes now existing.

By way purely of indication and not exhaustively, the present invention relates particularly to the location of ganglia such as those encountered in the case of breast cancer, genital cancer, cancer of the bladder, of the endocrine glands and the neuroendocrines, and colorectal cancer.

In particular, the present invention permits the per-operative visualization (in an open field or endoscopically) of the lymphatic draining network of an organ, location of the so-called "sentinel" ganglia, the extemporaneous histopathological characterization of tissues, the quantitative cartography and visualization, particularly of the lymphatic network on an anatomical image of the operating field.

Thus, surgical therapeutics and prognostic of a tumor require the per-operative exploration of the lymphatic chain of the organ and its anatomical environment because it is responsible for the diffusion of metastatic tumor cells, said exploration implying the location and/or detection particularly of the sentinel ganglia which represent the first line of this drainage system.

Thanks to the device and to the process according to the present invention, the early analysis of the lymphatic draining system permits appreciating in a very precise and reliable way the degree of spreading of the cancer and determining the location and extent of possible mutilating ablation of the ganglia chain, followed by the practice of supplemental chemotherapy or on the contrary, in the case of a negative result, conservative surgery.

Thus, the invention provides particularly an automatic device for the quantification of data, their initialization and editing in real time of an operational account in the form of the printing of data on an anatomical image of the operating field.

Of course, the invention is not limited to the embodiments described and shown in the accompanying drawing. Modifications remain possible, particularly as to the construction of the various elements or by substitution of technical equivalents, without thereby departing from the scope of protection of the invention.

What is claimed is:

1. Device for pre-operative location of marked tissues, which comprises at least one probe (1) having an elongated shape and integrating at least two of three types of detection means selected from the group comprised by:

at least one means (1) for the detection of radioactive radiation (3) emitted by tissues (4) marked with isotopes or radioactive colloids, generating a corresponding representative electrical signal (5);

at least one optical detection means comprising at least one means (6) for emitting luminous radiation toward the tissues (4) and at least one means (7) for receiving and transmitting luminous radiation (8) reflected or emitted by fluorescence or luminescence by said tissues (4) marked by vital colorants toward at least one means for conversion (9) of said recovered luminous radiation (8) into a corresponding electrical signal (10);

a means (15) for detecting magnetization or measuring magnetic susceptibility of the tissues (4) marked by superparamagnetic substances, generating a corresponding representative electrical signal (16);

and in addition to said at least two types of detection means, means for transmitting or conveying said electrical signals (5, 10, 16) and at least one electronic means (11) for processing electrical signals (5, 10, 16) conveyed by the last-named means, so as to display, superimpose, inlay and/or edit a reconstituted image (12), at least partial, of the tissues (4) marked by said colorants and simultaneously supplying a physically perceptible expression (12') of the representative electrical signal (5) delivered by the detection means (2) of the radioactive radiation (3) emitted by the radioactively marked tissues (4) and/or of the representative electrical signal (16) delivered by the means (15) for detecting the magnetization or measuring the magnetic susceptibility of the tissues (4) marked by superparamagnetic substances.

2. Device according to claim 1, characterized in that the probe (1) comprises means (2) for detecting radioactive radiation (3) and at least one optical detection means (6, 7).

3. Device according to claim 1, characterized in that the probe (1) comprises means (15) for detecting magnetization or for measuring magnetic susceptibility and at least one optical detection means (6, 7).

4. Device according to claim 1, characterized in that the probe (1) comprises means (2) for detecting radioactive radiation (3), means (15) for measuring magnetic susceptibility and at least one optical detection means (6, 7).

5. Device according to claim 1, characterized in that it comprises moreover means (14) for storing in digital form data relative to one or several reconstituted images (12) and to said representative electrical signals (5, 16) generated simultaneously, on an electronic storage support, such as a computer memory, as well as if desired data relating to one or more anatomical images (12") of the operating field enclosing the marked tissues (4), taken previously or subsequently.

6. Device according to claim 1, characterized in that the physically perceptible expression (12') of the representative electrical signal or signals (5, 16), simultaneously with the display of the reconstituted image (12), takes place in a sonic manner, for example by a loudspeaker or the like.

7. Device according to claim 1, characterized in that the perceptible physical expression (12') of the representative electrical signal or signals (5, 16), simultaneously with the display of a reconstituted image (12), takes place in a visual manner, for example by the display or editing of said reconstituted image (12) and if desired of the corresponding anatomical image (12").

8. Device according to claim 7, characterized in that the physically perceptible expression (12') of the representative electrical signal or signals (5, 16), simultaneous with the display of the reconstituted image (12), takes place on the screen (13) serving to display said reconstituted image (12) and if desired the corresponding anatomical image (12").

9. Device according to claim 1, characterized in that the detection means (2) of the radioactive radiation (3) is a gamma ray detector or x-ray detector.

10. Device according to claim 1, characterized in that the luminous emission means (6) is a laser.

11. Device according to claim 10, characterized in that the laser (6) used emits in a range of wavelengths comprised between 4,000 and 10,000 angstroms.

12. Device according to claim 1, characterized in that the means (7) for reception and transmission of the luminous radiation (8) reflected by the marked tissues (4) is an optical fiber or a bundle of fibers, at least partially, and preferably entirely, integrated into the elongated probe (1) and associated with a device for detecting and optically focusing (7'), such as for example a lens.

13. Device according to claim 1, characterized in that the conversion means (9) of said reflected luminous radiation (8) into an electrical signal (10) is a CCD camera or a detector of luminous radiation of the opto-electronic converter type, as the case may be associated with a photomultiplier.

14. Device according to claim 1, characterized in that the electronic means (11) for processing electrical signals (5, 10, 16) for the display, preferably in real time, of a reconstituted image (12) of the marked tissues (4) on a screen (13), if desired by superimposition of an anatomical image (12") separately acquired, is a computer workstation.

15. Device according to claim 14, characterized in that the computer workstation (11) is moreover provided with a means (13') for printing reconstituted images (12) and/or processed data relating to the electrical signals (5, 10, 16).

16. Device according to claim 1, characterized in that the elongated probe (1) is an endoscopic probe.

17. Process for locating tissues previously marked with radioactive isotopes, with vital colorants and/or with superparamagnetic substances, in particular for the location of tumors, using the device according to claim 1, characterized in that it comprises essentially the following steps:

carrying out a first empirical marking of the zone or zones of tissues to be examined, producing a first series of reconstituted images (12) of the tissues (4) marked by said colorants in the precedingly determined zone or zones or in the suspected zone or zones, so as to determine the approximate contours of said zone or zones to be examined in greater detail, within the previously determined contours, proceeding with a series of measurements by the detection of the radioactive radiation (3) emitted by said radioactively marked tissues (4) and/or with the detection of the supply or measurement of the magnetic susceptibility of said magnetically marked tissues (4) so as to determine more precisely the contours of the zones representing peaks of radioactivity and/or of magnetic characteristics, and producing a second series of reconstituted images (12) of the marked tissues (4) in the zone or zones determined in the preceding step so as to obtain one or more reconstituted images (12) with precise contours, of said zone or zones of marked tissues (4), particularly for the display, temporary storage, editing, filing and/or ultimate processing, for example electronic, of said reconstituted image or images (12) and the visible expression or expressions of the representative signal or signals (5, 16).

18. Process according to claim 17, characterized in that the first empirical marking takes place in a manner visible to the naked eye.

19. Process according to claim 17, characterized in that the first empirical marking, or a second empirical marking, is carried out by palpation of the zones of tissues.

20. Process according to claim 17, characterized in that it consists in also carrying out the taking of anatomical images (12") of the operating field enclosing the zone of tissues to be examined and particularly the marked tissues (4) to be located, before taking the first series of reconstituted images (12) or after taking the second series of reconstituted images (12), these latter, as well as if desired the visible expression or expressions (12') of the representative electrical signal or signals (5, 16), being added by inlaying or superimposition onto said anatomical image or images (12").

* * * * *